(12) United States Patent
Shimada et al.

(10) Patent No.: US 6,994,697 B2
(45) Date of Patent: Feb. 7, 2006

(54) PULL-ON DISPOSABLE DIAPER

(75) Inventors: Takaaki Shimada, Kagawa-ken (JP); Seiji Suzuki, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 405 days.

(21) Appl. No.: 09/772,572

(22) Filed: Jan. 30, 2001

(65) Prior Publication Data

US 2002/0004655 A1 Jan. 10, 2002

(30) Foreign Application Priority Data

Jan. 31, 2000 (JP) .................................... 2000-022201

(51) Int. Cl.
*A61F 13/15* (2006.01)

(52) U.S. Cl. .................................. 604/385.13; 604/396
(58) Field of Classification Search .............. 604/385.1, 604/385.19, 385.201, 386, 389, 390, 385.13
See application file for complete search history.

(56) References Cited

U.S. PATENT DOCUMENTS

| | | | | |
|---|---|---|---|---|
| 4,911,702 A | * | 3/1990 | O'Leary et al. | 604/389 |
| 5,100,399 A | * | 3/1992 | Janson et al. | 604/385.21 |
| 5,108,384 A | * | 4/1992 | Goulait | 604/389 |
| 5,851,205 A | * | 12/1998 | Hisada et al. | 604/389 |
| 6,063,067 A | * | 5/2000 | Takizawa et al. | 24/452 |
| 6,210,386 B1 | * | 4/2001 | Inoue | 604/385.01 |
| 6,475,205 B2 | * | 11/2002 | Shimada et al. | 604/385.13 |

FOREIGN PATENT DOCUMENTS

| | | |
|---|---|---|
| DE | 196 54 456 A1 | 12/1996 |
| EP | 0 815 820 A2 | 1/1998 |
| EP | 0 875 226 A2 | 11/1998 |
| EP | 0 890 351 A2 | 1/1999 |
| EP | 0 965 317 A2 | 12/1999 |
| JP | 9-253123 | 9/1997 |
| JP | 9-253124 | 9/1997 |

OTHER PUBLICATIONS

Patent Abstracts of Japan, vol. 1998, No. 1, Jan. 30, 1998 & JP 09 253123 A (Uni Charm Corp), Sep. 30, 1997.
Patent Abstracts of Japan, vol. 1998, No. 1, Jan. 30, 1998 & JP 09 253124 A (Uni Charm Corp), Sep. 30, 1997.

* cited by examiner

*Primary Examiner*—John J. Calvert
*Assistant Examiner*—C. Lynne Anderson
(74) *Attorney, Agent, or Firm*—Butzel Long

(57) ABSTRACT

A pull-on disposable diaper that is provided in parallel to transversely opposite side edges thereof in its rear waist region with fastening tape strips. The tape strips are configured in its rolled up state for disposable after the diaper has been used. Each of the tape strips includes longitudinally opposite end regions firmly bonded to respective peripheral edges of the diaper's waist-opening and leg-openings. An intermediate region of each of the fastening tape strips includes an adhesive region on its inner surface which is adapted to be separably bonded to the outer surface of the diaper when rolled up for disposal.

4 Claims, 5 Drawing Sheets

PULL-ON DISPOSABLE DIAPER

BACKGROUND OF THE INVENTION

This invention relates to a pull-on disposable diaper provided with fastening tape to fasten the diaper in its rolled up state for disposal after the diaper has been used.

Japanese Patent Application Publication A NO. 1997-253123 describes a disposable diaper comprising a topsheet, a backsheet and a core disposed between these two sheets so as to configure a front waist region, a rear waist region and a crotch region extending between these two waist regions. The front or rear waist region is provided on the outer surface of the backsheet with a single strip of fastening tape adapted to fasten the used diaper in its rolled up state for disposal. More specifically, the strip of fastening tape extends circumferentially of the diaper and has its longitudinally middle portion fixed to the diaper and its longitudinally opposite end portions folded up so that these end portions may be unfolded when it is desired to use this strip of fastening tape. The longitudinally opposite end portions are coated with pressure-sensitive adhesive by means of which these end portions are maintained in folded up state.

Japanese Patent Application Publication A No. 1997-253124 describes a disposable diaper comprising a topsheet, a backsheet and a core disposed between these two sheets so as to configure a front waist region, a rear waist region and a crotch regions extending between these two waist region. The front or rear waist region is provided on the outer surface of the backsheet with fastening tape adapted to fasten the used diaper in its rolled up state for disposal.

In this diaper of prior art, the fastening tape comprises at least two strips of adhesive tape extending in parallel to each other circumferentially of the diaper.

For disposal, these diapers of prior art are similar to each other in that the strip(s) of fastening tape is or are wound around the outer peripheral surface of the diaper which has been used and rolled up from its transversely opposite side edges and fixed to the outer peripheral surface of the used diaper.

It is possible for these diapers described in the above-mentioned publications to hold the used diaper in its rolled up state by fastening the rolled up diaper substantially at a middle level of the diaper. However, it is impossible for these diapers to close the waist-opening of the diaper utilizing the strip(s) of fastening tape. Even after the used diaper has tightly been rolled up from its transversely opposite side edges, the waist-opening remains free and it is concerned that excretion itself or its odor might leak through the waist-opening.

SUMMARY OF THE INVENTION

It is an object of this invention to provide a pull-on disposable diaper adapted to be held in its rolled up state for disposal without any anxiety that excretion itself or its odor might leak through the waist-opening and/or the leg-openings.

According to this invention, there is provided a pull-on disposable diaper comprising a liquid-pervious topsheet, a liquid-impervious backsheet and a liquid-absorbent core disposed between the topsheet and the backsheet to define a front waist region, a rear waist region and a crotch region extending between the front and rear waist regions, the front and rear waist regions being placed upon each other with the topsheet inside along transversely opposite side edges of the diaper to define a waist-opening and a pair of leg-openings and wherein the diaper having an elastic stretchability circumferentially of the openings is provided on an outer surface of the backsheet with fastening tape strips adapted to hold the diaper in a rolled up state thereof for disposal after the diaper has been used.

This invention further comprising fastening tape strips extending in the longitudinal direction in parallel to the transversely opposite side edges in at least one of the front and rear waist regions, each of the fastening tape strips having longitudinally opposite end regions thereof bonded to the diaper in vicinity of respective peripheral edges of the waist-opening and the leg-openings and an intermediate region extending between the longitudinally opposite end regions and defining on an inner surface thereof an adhesive region adapted to be separably bonded on an outer peripheral surface of the diaper rolled up for disposal.

In the pull-on disposable diaper according to this invention, the longitudinally opposite end regions have their longitudinally opposite ends bonded to the respective peripheral edges of the waist-opening and the leg-openings in contiguousness to the elastic members secured under tension to the respective peripheral edges of the waist-opening and the leg-openings so that the respective elastic members may be stretched outward transversely of the diaper as the respective fastening tape strips are pulled outward transversely of the diaper.

The fastening tape strips wound and anchored on the outer peripheral surface of the rolled up diaper will hold the diaper in its rolled up state and tensile force generated in the respective elastic members maintains the waist-opening and the leg-openings in closed state. As a result, there is no anxiety that these openings might be loosen and excretion or its odor might leak through these openings.

With the embodiment of the diaper in which the fastening tape strips extend to describe curves which are convex outward transversely of the diaper, the fastening tape strips can be anchored on the outer peripheral surface of the diaper over a larger area and more firmly than in the case of the fastening tape strips extending rectilinearly.

DETAILED DESCRIPTION OF THE PREFERRED EMBODIMENTS

Details of a pull-on disposable diaper according to this invention will be more fully understood from the description given hereunder with reference to the accompanying drawings.

Figure 1:
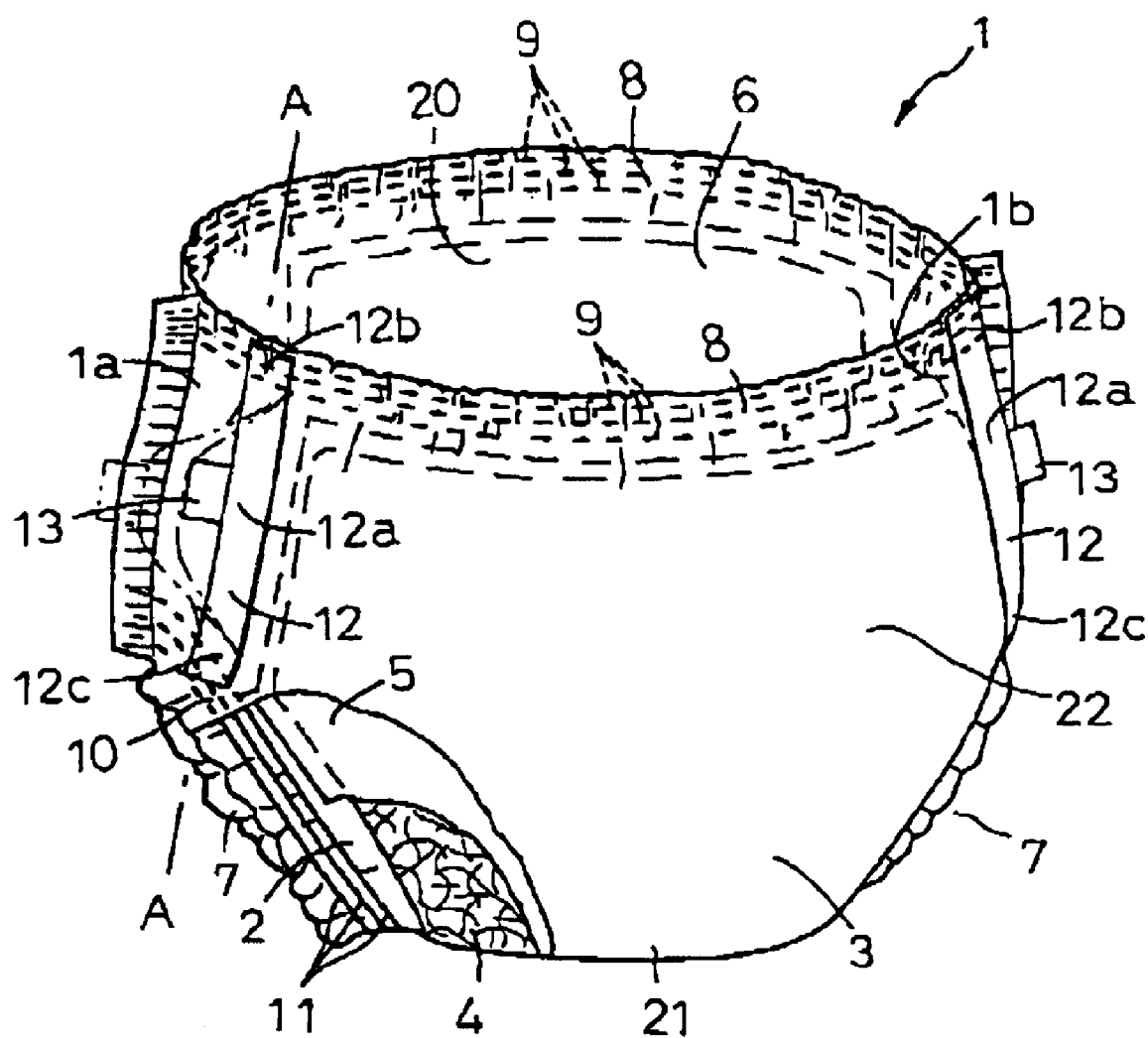
FIG. 1 is a partially cutaway perspective view depicting one embodiment of a pull-on disposable diaper according to this invention as viewed from the rear waist region side.
Figure 2:
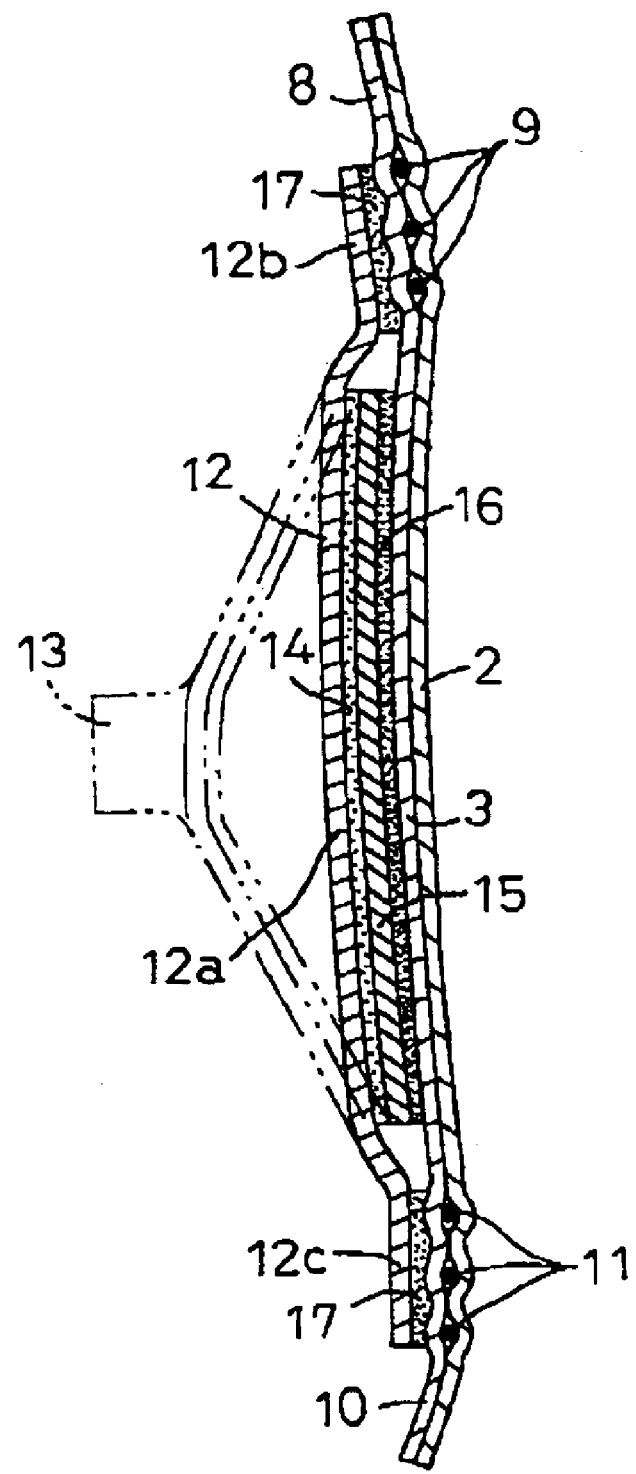
FIG. 2 is a sectional view taken along line A—A in FIG. 1.

FIG. 1 is a partially cutaway perspective view depicting one embodiment of a pull-on disposable diaper 1 according to this invention as viewed from the side of a rear waist region and FIG. 2 is a sectional view taken along line A—A in FIG. 1. Referring to FIG. 1, one of fastening tape strips 12 is illustrated as it has been peeled off from a release sheet 15 as indicated by chain line. The diaper 1 basically comprises a liquid-pervious topsheet 2, a liquid-impervious backsheet 3 and a liquid-absorbent core 4 disposed between the topsheet 2 and the backsheet 3 and entirely covered with and bonded to a water-pervious tissue paper 5. The tissue paper 5 is bonded to the inner surface of at least one of the topsheet 2 and the backsheet 3.

The diaper 1 is longitudinally configured by a front waist region 20 a rear waist region 22 and a crotch region 21 extending between the front and rear waist regions 20, 22. In this diaper 1, transversely opposite side edges 1a, 1b longitudinally extending in the front and rear waist regions 20, 22, respectively, are put flat together and bonded together to define a waist-opening 6 and a pair of leg-openings 7.

A plurality of elastically stretchable members 9 extend entirely along a peripheral edge 8 of the waist-opening between the topsheet 2 and the backsheet 3 and are secured under tension to the inner surface of at least one of the topsheet and the backsheet 3. Similarly, a plurality of elastically stretchable members 11 extend entirely along a peripheral edge 10 of each leg-opening 7 between the topsheet 2 and the backsheet 3 and are secured under tension to the inner surface of at least one of the topsheet 2 and the backsheet 3. In the diaper 1, the respective peripheral edges 8, 10 of the waist-opening 6 and the leg-openings 7 have an elastic stretchability circumferentially of these openings 6, 7. In the state shown by FIG. 1, the elastic members 9, 11 have been relieved of the tension and a plurality of gathers are formed along the respective peripheral edges 8, 10 of the waist-opening 6 and the leg-openings 7.

In the vicinity of the transversely opposite side edges 1a, 1b of the rear waist region 22, the backsheet 3 is provided on its outer surface with a pair of fastening tape strips 12 used to hold the used diaper 1 in its rolled up state for disposal. These fastening tape strips 12 are formed by flexible but non-stretchable plastic sheets.

Each of the fastening tape strips 12 comprises longitudinally opposite ends regions 12b, 12c lying on the peripheral edge 8 of the waist-opening 6 and on the peripheral edge 10 of the leg-opening 7, respectively, and an intermediate region 12a extending between the end portions 12b, 12c. The end regions 12b, 12c are contiguous to the elastic members 9, 11 attached to the peripheral edges 8, 10 of the waist-opening 6 and the leg-opening 7, respectively, and bonded to the outer surface of the backsheet 3 by means of adhesive 17. While the longitudinally opposite end regions $12b_1$, 12c are preferably contiguous to two or more of the elastic members 10, 11 respectively associated with the waist-opening 6 and the leg-openings 7, it suffices that these end regions 12b, 12c are contiguous to at least one of these elastic members 9, 11, respectively.

The intermediate region 12a of the fastening tape strip 12 is coated on its inner surface with pressure-sensitive adhesive 14. A handling tip region 13 is branched outward transversely of the diaper 1 from the intermediate region 12a of the fastening tape strip 12. The intermediate region 12a of the fastening tape strip 12 is destined to be separably anchored on the outer surface of the backsheet 3 after the used diaper 1 has been rolled up for disposal.

In the vicinity of the side edges 1a, 1b in the rear waist region 22, plastic release sheets 15 extending longitudinally of the diaper 1 are bonded to the outer surface of the backsheet 3 by means of adhesive 16. The respective intermediate regions 12a of the fastening tape strips 12 are temporarily bonded to the respective release sheets 15 by means of pressure-sensitive adhesive 14.

As indicated by chain lines in FIG. 1, the intermediate regions 12a of the fastening tape strips 12 are not bonded to the outer surface of the backsheet 3 and therefore deformable, e.g., flexible and twistable.

Figure 3:
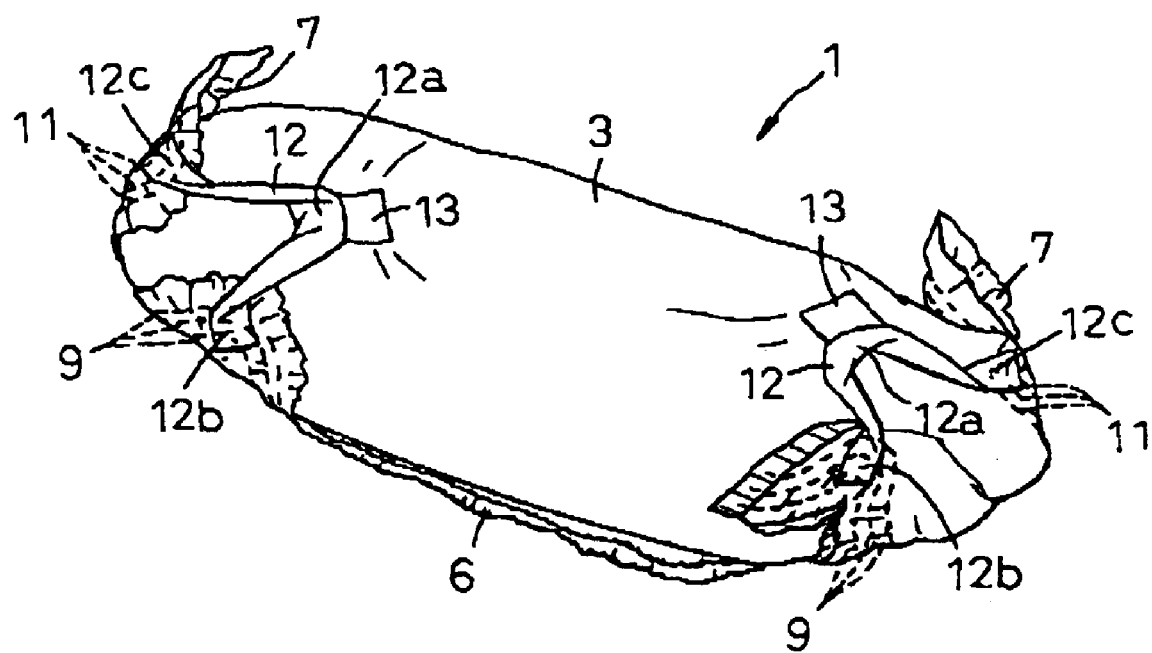
FIG. 3 is a perspective view depicting the diaper of FIG. 1 as rolled up for disposal.

FIG. 3 is a perspective view depicting the diaper 1 of FIG. 1 as rolled up for disposal. The diaper 1 is longitudinally rolled up from the crotch region 21 toward the waist-opening 6 with the front waist region 20 inside and the waist-opening 6 outside.

The fastening tape strips 12 are transversely wound around the outer peripheral surface of the rolled up diaper 1 and the intermediate regions 12a of the fastening tape strips 12 are anchored on the outer surface of the backsheet 3 by means of pressure-sensitive adhesive 14. Referring to FIG. 3, the respective peripheral edges 8, 10 of the waist-opening 6 and the leg-openings 7 are partially folded inward transversely of the diaper 1.

To fasten the rolled up diaper 1 by the fastening tape strips 12, the intermediate regions 12a thereof are peeled off from the release sheets 15 with the handling tips 13 held by fingers and then the intermediate regions 12a of the fastening tape strips 12 are pressed against the outer surface of the backsheet 3 with the fastening tape strips 12 being pulled outward transversely of the diaper 1.

The elastic members 9 associated with the waist-opening and the elastic members 11 associated with the leg-openings to which the longitudinally opposite end regions 12b, 12c of the respective fastening tape strips 12 are contiguous are stretched outward transversely of the diaper 1 as the respective fastening tape strips 12 are pulled outward transversely of the diaper 1. Tensile force generated in the respective elastic members 9, 11 stretched in this manner places the respective peripheral edges 8, 10 of these openings 6, 7 under tension and thereby tends to close these openings 6, 7. In this way, the used diaper 1 is held by the respective fastening tape strips 12 in its rolled up state and at the same time the waist-opening 6 and the leg-openings 7 are closed under the tensile force generated in the respective elastic members 9, 11. Accordingly, there is no anxiety that these openings 6, 7 might be loosen and excretion or its odor might leak through these openings 6, 7.

Figure 4:
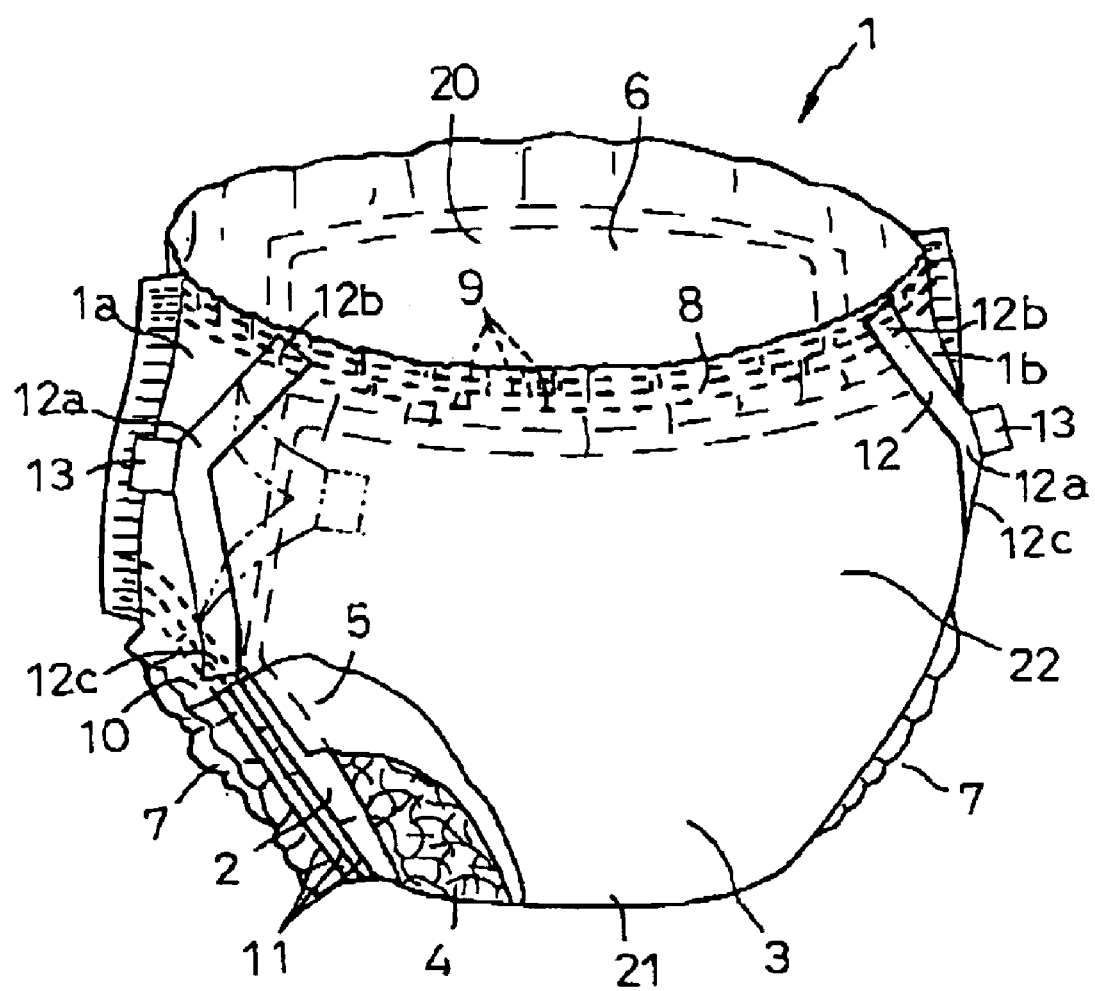
FIG. 4 is a view similar to FIG. 1 depicting another embodiment of the diaper as viewed from the rear waist region side.

FIG. 4 is a partially cutaway view similar to FIG. 1 depicting another embodiment of the diaper 1, in which one of fastening tape strips 12 is illustrated as it has been peeled off from a release sheet (not shown) as indicated by imaginary line. The diaper 1 basically comprises a liquid-pervious topsheet 2, a liquid-impervious backsheet 3 and a liquid-absorbent core 4 disposed between the topsheet 2 and the backsheet 3 and covered with and bonded to a water-pervious tissue paper 5. In this diaper 1, transversely opposite side edges 1a, 1b in the front and rear waist regions 20, 22, respectively, are put flat together and bonded together to define a waist-opening 6 and a pair of leg-openings 7.

Along the peripheral edge 8 of the waist-opening 6 in the rear waist region 22, a plurality of elastic members 9 are disposed between the topsheet 2 and the backsheet 3 and secured under tension to the inner surface of at least one of the topsheet 2 and the backsheet 3. Entirely along the respective peripheral edges 10 of the leg-openings 7, a plurality of elastic members 11 are disposed between the topsheet 2 and the backsheet 3 and secured under tension to the inner surface of at least one of the topsheet 2 and the backsheet 3.

In the vicinity of the transversely opposite side edges 1a, 1b of the rear waist region 32, the backsheet 3 is provided on its outer surface with a pair of fastening tape strips 12 longitudinally extending in parallel to the side edges 1a, 1b. These fastening tape strips 12 are formed by flexible but non-stretchable plastic sheets each comprising longitudinally opposite end regions 12b, 12c and an intermediate region 12a. The intermediate region 12a extends to describe a curve which is convex outward transversely of the diaper 1.

The longitudinally opposite end regions 12b, 12c of the fastening tape strip 12 are contiguous to the elastic members 9, 11 which are, in turn, attached to the respective peripheral edges 8, 10 of the waist-opening 6 and the leg-openings 7, respectively, and bonded to the outer surface of the backsheet 3 by means of adhesive (not shown). The intermediate regions 12a of the fastening tape strips 12 are coated with pressure-sensitive adhesive (not shown). The handling tip regions 13 extend outward transversely of the diaper 1 from the respective intermediate regions 12a of the fastening tape strips 12.

In the vicinity of the side edges 1a, 1b in the rear waist region 22, plastic release sheets extending longitudinally of the diaper 1 are bonded to the outer surface of the backsheet 3 by means of adhesive (not shown). The respective intermediate regions 12a of the fastening tape strips 12 are temporarily bonded to the respective release sheets by means of pressure-sensitive adhesive.

Figure 5:
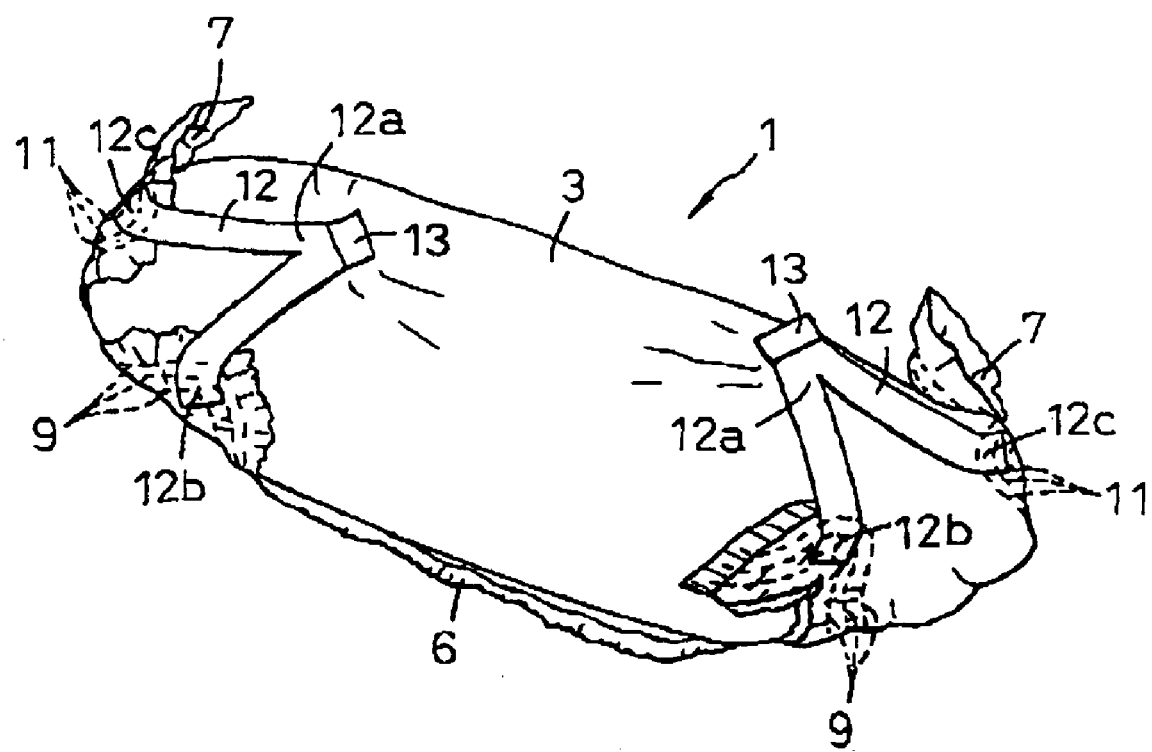
FIG. 5 is a view similar to FIG. 3 depicting the diaper of FIG. 4 as rolled up for disposal.

FIG. 5 is a perspective view depicting the diaper 1 of FIG. 4 as rolled up for disposal. The diaper 1 is rolled up from the crotch region 21 toward the waist-opening 6 with the front waist region 20 lying inside and the waist-opening 6 lying outside.

The fastening tape strips 12 are transversely wound around the outer peripheral surface of the rolled up diaper 1. Thereupon, the intermediate regions 12a of the fastening tape strips 12 are anchored on the outer surface of the backsheet 3 by means of pressure-sensitive adhesive. In FIG. 5, portions of the peripheral edges 8, 10 of the waist-opening 6 and the leg-openings are folded laterally inside the diaper.

The elastic members 9 associated with the waist-opening and the elastic members 11 associated with the leg-openings to which the longitudinally opposite end regions 12b, 12c of the respective fastening tape strips 12 are contiguous are stretched outward transversely of the diaper 1 as the respective fastening tape strips 12 are pulled outward transversely of the diaper 1. Tensile force generated in the respective elastic members 9, 11 stretched in this manner places the respective peripheral edges 8, 10 of these openings 6, 7 under tension and thereby tends to close these openings 6, 7. In this way, the used diaper 1 is held by the respective fastening tape strips 12 in its rolled up state and at the same time the waist-opening 6 and the leg-opening 7 are closed under the tensile force generated in the respective elastic members 9, 11. Accordingly, there is no anxiety that these openings 6, 7 might be loosen and excretion or its odor might leak through these openings 6, 7.

With the diaper 1 according to this invention, the fastening tape strips 12 extending to describe curves enable the fastening area to the outer surface of the backsheet 3 achieved by the respective tape strips 12 to be larger than that achieved by the rectilinearly extending tape strips. In this way, the fastening effect of the tape strips 12 is improved.

The topsheet 2 may be formed from a liquid-pervious sheet such as a nonwoven fabric or a porous plastic film, preferably from a liquid-pervious hydrophilic sheet. The backsheet 3 may be formed from a hydrophobic nonwoven fabric, a liquid-impervious plastic film or a laminated sheet consisting of a hydrophobic nonwoven fabric and a plastic film, preferably from a breathable liquid-impervious sheet. It is also possible to form the backsheet 3 using a composite nonwoven fabric (SMS nonwoven fabric) comprising a sheet of melt blown nonwoven fabric being high in water resistance and two sheets of spun bond nonwoven fabric being high in strength as well as in flexibility so that opposite sheet surfaces of the melt blown nonwoven fabric may be sandwiched between the respective sheet surfaces of the spun bond nonwoven fabric.

The nonwoven fabric may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric. Component fiber of the nonwoven fabric may be selected from a group including polyolefine fiber, polyester fiber, polyamide fiber or conjugated fiber, for example, polyethylene/polypropylene or polyester conjugated fiber.

The core 4 is a mixture of fluff pulp and high absorption polymer particles compressed to a desired thickness. Bonding or attaching of the core 4, the sheets 2, 3, 15, the tape strips 12 and the elastic members 9, 11 may be carried out using suitable adhesive such as hot melt adhesive or pressure-sensitive adhesive or heat-sealing technique.

The fastening tape strip 12 may be formed from an inelastic plastic sheet, elastomer such as synthetic or natural rubber having a degree of elastic stretchability or nonwoven fabric to which such elastomer has been secured under tension. In the case of the stretchable fastening tape strip 12, tensile force generated in the elastic members 9, 11 associated with the waist-opening and the leg-openings, respectively, cooperate with tensile force generated in the fastening tape strip 12 to improve the effect under which the waist-opening 6 and the leg-openings 7 can be held in a closed state.

It is possible without departing from the scope of this invention to attach the fastening tape strips 12 to the side edges 1a, 1b of the front waist region 20, respectively. It is also possible to attach one of these fastening tape strips 12 to one side edge 1a of the diaper 1 in the rear waist region 22 and to attach the other fastening tape strip 12 to the other side edge 1b of the diaper 1 in the front waist region 20.

It is possible to dispose the longitudinally opposite end regions 12b, 12c of the fastening tape strip 12 between the backsheet 3 and the tissue paper 5 and to bond them to at least one of the backsheet 3 and the tissue paper 5.

While the elastic members 9 associated with the waist-opening may be secured under tension to the diaper 1 along the peripheral edge 8 of the waist-opening 6 at least one of the front and rear waist regions 20, 22, it is essential for the fastening tape strips 12 to be provided in the vicinity of the side edges 1a, 1b and the waist region provided with the elastic members 9 associated with the waist-opening 6.

In the case of the backsheet 3 formed from a nonwoven fabric, it is also possible to provide the fastening tape strips 12 on the inner surfaces of the respective intermediate regions 12a thereof with hook members instead of being coated with pressure-sensitive adhesive 15 so that the hook members are engaged with fibers of the nonwoven fabric to anchor the respective intermediate regions 12a of the fastening tape strips 12 on the outer surface of the backsheet 3. When the respective intermediate regions 12a of the fastening tape strips 12 are provided with such hook members, the loop members may be used in the place of the release sheets 15 firmly bonded to the outer surface of the backsheet 3.

What is claimed is:

1. A pull-on disposable diaper comprising:

a liquid-pervious topsheet;

a liquid-impervious backsheet;

a liquid-absorbent core disposed between said topsheet and said backsheet;

a front waist region having transversely opposite side edges;

a rear waist region having transversely opposite side edges; and a crotch region extending between said front and rear waist regions, said front and rear waist regions being placed upon each other with said topsheet inside and said transversely opposite side edges of each of said front and rear waist regions being bonded directly together along their entire lengths to form a waist-opening and a pair of leg-openings, said diaper having an elastic stretchability circumferentially of said wait-opening and said leg-openings, said diaper further comprising fastening tape strips for holding said diaper in a rolled up state for disposal after said diaper has been used, said fastening tape strips being provided on an outer surface of said liquid-impervious backsheet and extending in a longitudinal direction of said diaper in parallel to said transversely opposite side edges in at least one of said front and rear waist regions, each of the fastening tape strips having longitudinally opposite end regions thereof bonded to the diaper in a vicinity of respective peripheral edges of said waist-opening and said leg-openings and an intermediate region extending between said longitudinally opposite end regions and including on an inner surface thereof an adhesive region adapted to be separately bonded on the outer peripheral surface of said diaper when said diaper is rolled up for disposal, said intermediate region of each of said fastening tape strips describing an angle having an apex which apex projects outward transversely of said diaper.

2. The diaper according to claim 1, wherein said intermediate region of each of the fastening tape strips is temporarily bonded to the outer surface of said backsheet by means of said adhesive region provided in a vicinity of said transversely opposite side edge regions.

3. The diaper according to claim 1, wherein each of said fastening tape strips is made of a flexible but non-stretchable plastic sheet.

4. The diaper according to claim 1, wherein said intermediate region of each of said fastening tapes strips is coated on an inner surface thereof with a pressure-sensitive adhesive.

* * * * *